(12) United States Patent
Min et al.

(10) Patent No.: US 11,780,880 B2
(45) Date of Patent: Oct. 10, 2023

(54) HIGH-ACTIVITY MEMORY-IMPROVING DERIVATIVE PEPTIDE AND USE THEREOF

(71) Applicant: Jilin Agricultural University, Changchun (CN)

(72) Inventors: Weihong Min, Changchun (CN); Hongyan Lu, Changchun (CN); Chunlei Liu, Changchun (CN); Ji Wang, Changchun (CN); Li Fang, Changchun (CN)

(73) Assignee: JILIN AGRICULTURAL UNIVERSITY, Changchun (CN)

( * ) Notice: Subject to any disclaimer, the term of this patent is extended or adjusted under 35 U.S.C. 154(b) by 0 days.

(21) Appl. No.: 17/936,424

(22) Filed: Sep. 29, 2022

(65) Prior Publication Data

US 2023/0104490 A1    Apr. 6, 2023

(30) Foreign Application Priority Data

Sep. 30, 2021 (CN) .......................... 202111159425.3

(51) Int. Cl.
  *C07K 7/06* (2006.01)
  *A61P 25/28* (2006.01)
  *A61K 38/00* (2006.01)

(52) U.S. Cl.
  CPC ................ *C07K 7/06* (2013.01); *A61P 25/28* (2018.01); *A61K 38/00* (2013.01)

(58) Field of Classification Search
  None
  See application file for complete search history.

(56) References Cited

PUBLICATIONS

Lu et al. "Pine nut antioxidant peptides ameliorate the memory impairment in a scopolamine-induced mouse model via SIRT3-induced synaptic plasticity" Food & Function 12:8026-8036. (Year: 2021).*

* cited by examiner

*Primary Examiner* — Sudhakar Katakam
*Assistant Examiner* — Zachary J Miknis
(74) *Attorney, Agent, or Firm* — McDonnell Boehnen Hulbert & Berghoff LLP

(57) ABSTRACT

The present disclosure provides a high-activity memory-improving derivative peptide and use thereof in preparation of memory-improving medicaments, health care products or foods, and belongs to the field of biotechnology. According to the present disclosure, proline 3 (Pro3) of a pine nut high-activity memory-improving peptide, WYPGK, is completely substituted with common amino acids to obtain 19 derivative peptides, and the derivative peptides are subjected to molecular docking with mitochondrial deacetylase sirtuin 3 and are screened by binding energy to obtain derivative peptides WYEGK, WYKGK, WYSGK, and WYFGK; solid-phase chemical synthesis is conducted by a peptide synthesizer; the derivative peptides are purified by reversed phase high performance liquid chromatography (RP-HPLC) and prepared by electrospray ionization mass spectrometry (ESI-MS). Morris water maze for scopolamine-induced memory impairment model mice demonstrates that the derivative peptides have high memory-improving activity.

12 Claims, 11 Drawing Sheets
Specification includes a Sequence Listing.

HIGH-ACTIVITY MEMORY-IMPROVING DERIVATIVE PEPTIDE AND USE THEREOF

CROSS REFERENCE TO RELATED APPLICATION

This patent application claims the benefit and priority of Chinese Patent Application No. 202111159425.3, filed with the China National Intellectual Property Administration on Sep. 30, 2021, the disclosure of which is incorporated by reference herein in its entirety as part of the present application.

REFERENCE TO SEQUENCE LISTING

A computer readable XML file entitled "GWP20220901840_seqlist.xml", that was created on Nov. 28, 2022, with a file size of about 21,661 bytes, contains the sequence listing for this application, has been filed with this application, and is hereby incorporated by reference in its entirety.

TECHNICAL FIELD

The present disclosure belongs to the field of biotechnology, and in particular relates to a high-activity memory-improving derivative peptide and use thereof in preparation of memory-improving medicaments, health care products or foods.

BACKGROUND

Oxidative stress is the imbalance of the oxidative system caused by the accumulation of excess free radicals in the body. In recent years, the occurrence and development of oxidative stress are aggravated with the increased number of the aging population in China, the acceleration of the pace of life of the middle-aged and young, and the increase in all kinds of mental stress. Mitochondria are the main sites for redox reactions and energy metabolism in cells. Also, mitochondria produce reactive oxygen species (ROS) and are primary targets for being attacked by ROS. Damaged mitochondria will release a large quantity of ROS, attenuate neuronal mitophagy, induce neuroinflammation and apoptosis, cause dysfunction of synaptic plasticity, reduce the number and density of synapses, destroy the blood-brain barrier (BBB) integrity, and cause BBB leakage, further leading to a decline in learning and memory. And with age, memory function deteriorates rapidly, generally from initial memory disorder to aphasia, agnosia, apraxia, visuospatial impairment, executive dysfunction, personality disorders, and other comprehensive dysfunctions, and in more severe cases, dementia. Therefore, targeted intervention in mitochondrial homeostasis and maintenance of the body's oxidative defense balance can be an effective strategy for neuroprotection and improving learning and memory impairment. In recent years, food-derived proteins and food processing by-products have received extensive attention for their potential in the preparation of bioactive peptides, especially memory-improving peptides based on high antioxidant activity.

Antioxidant peptides are a group of natural bioactive peptides, usually composed of 3-15 amino acids, with strong antioxidant activity, and their activity is affected by the composition, quantity, sequence and structure of amino acids. Antioxidant peptides are absorbed and utilized by the human body because of their small molecular weights and their penetration through the cell membrane. Moreover, antioxidant peptides have high safety and significant advantages in absorption rate and biological function. Modern nutritional studies have found that most of the proteins ingested by humans are digested and absorbed in the form of low molecular weight peptides after the action of digestive enzymes, which are higher than free amino acids in biological potency and nutritional value. The present disclosure shows that a pine nut-derived antioxidant peptide WYPGK (SEQ ID NO: 1) can activate SIRT3 to improve the synaptic plasticity of mice with scopolamine-induced memory impairment, and ameliorate the learning and memory of the mice. In addition, high-activity memory-improving peptides can be used as ingredients in food and drug formulations to prevent oxidative stress-related diseases and improve learning and memory. Also, high-activity memory-improving peptides can be used as food additives to inhibit the oxidation of food, and play an important role in the field of food and health care products.

The primary structure or spatial conformation of a bioactive peptide is the key to determining functional activity thereof. Currently, an active peptide is prepared by enzymatic hydrolysis, and its functional activity is limited by the primary structure of the raw protein. The development of derivative peptides is one of the effective strategies to solve the problems that restrict the development and application of active peptides, and further becomes an important development direction in the fields of food science and pharmacy in recent years. Not only can the modification of a high-activity memory-improving peptide confer excellent properties on a peptide molecule, but also can change the steric hindrance between amino acids and inhibit the hydrolysis of peptide bonds by proteases, thereby further improving the activity and stability of active peptides in vivo. Therefore, in the present disclosure, a peptide WYPGK (SEQ ID NO: 1), which significantly improves the learning and memory of scopolamine-induced model mice, is obtained through enzymatic hydrolysis, separation, purification, and structural identification from pine nut protein. On this basis, the amino acid composition of the active peptide is modified; furthermore, combined with the optimization and screening of antioxidant-related mitochondrial deacetylase SIRT3, a high-activity memory-improving derivative peptide is finally obtained to realize the use thereof in foods and medical care products.

SUMMARY

An objective of the present disclosure is to provide a high-activity memory-improving derivative peptide and use thereof in preparation of memory-improving medicaments, health care products or foods. The high-activity memory-improving derivative peptide belongs to a natural derivative peptide, which is highly safe, has high memory-improving and antioxidant activity, anti-acid-base stability, and gastrointestinal digestion stability.

The present disclosure provides a high-activity memory-improving derivative peptide, where an amino acid sequence thereof is one selected from the group consisting of Trp-Tyr-Glu-Gly-Lys (WYEGK, SEQ ID NO: 2), Trp-Tyr-Lys-Gly-Lys (WYKGK, SEQ ID NO: 3), Trp-Tyr-Ser-Gly-Lys (WYSGK, SEQ ID NO: 4), and Trp-Tyr-Phe-Gly-Lys (WYFGK, SEQ ID NO:5).

According to the high-activity memory-improving derivative peptide provided by the present disclosure, through Morris water maze for scopolamine-induced memory impairment model mice, escape latency significantly decreases from 70.74 s to 35.78-40.53 s, percent time spent in target quadrant increases from 24.24% to 32.19-36.22%, and frequency of platform crossing increases from 1.1 times to 3.1-3.8 times in mice of each of derivative peptide treatment groups compared with a model group.

According to the high-activity memory-improving derivative peptide provided by the present disclosure, an antioxidant capacity of the derivative peptide is determined by ABTS free radical scavenging assay and oxygen radical antioxidant capacity (ORAC) assay; at a derivative peptide concentration of 100 μM, ABTS free radical scavenging rate of the WYEGK (SEQ ID NO: 2), the WYKGK (SEQ ID NO: 3), the WYSGK (SEQ ID NO: 4), and the WYFGK (SEQ ID NO: 5) reaches 54.48%, 40.31%, 70.47%, and 36.56%, respectively, all of which are higher than reduced glutathione (GSH), namely 31.39%; ORAC values thereof reach 5,422.29, 3,681.50, 5,473.16, and 3,762.05 μmol TE/g, respectively, all of which are significantly higher than the GSH, namely 995.58 μmol TE/g, indicating that the high-activity memory-improving derivative peptide provided by the present disclosure has high antioxidant activity.

According to the high-activity memory-improving derivative peptide provided by the present disclosure, stability thereof is analyzed by pH stability, simulating gastric and intestinal digestion experiments. Experimental results show that the derivative peptide is hardly degraded under acid-base conditions (at pH 2 to 8), and retention rate of peptide content reaches at least 93.45% in simulated gastrointestinal digestion.

The high-activity memory-improving derivative peptide provided by the present disclosure can be used in preparation of memory-improving medicaments, health care products or foods; the medicaments, health care products or foods may further include other memory-improving and antioxidant active ingredients and/or acceptable excipients.

Compared with the prior art, the present disclosure has the following beneficial effects:

The present disclosure uses a pine nut-derived high-activity memory-improving peptide WYPGK (SEQ ID NO:1) as a template. On the basis of ensuring high activity of original N-terminal and C-terminal amino acids, proline 3 (Pro3) of the pine nut high-activity memory-improving peptide, WYPGK (SEQ ID NO:1), is completely substituted with 19 kinds of common amino acids, subjected to molecular docking with mitochondrial deacetylase sirtuin 3 (SIRT3) and screened to obtain derivative peptides WYEGK (SEQ ID NO: 2), WYKGK (SEQ ID NO: 3), WYSGK (SEQ ID NO: 4), and WYFGK (SEQ ID NO: 5) having better memory-improving and antioxidant activity, higher anti-acid-base stability and gastrointestinal digestion stability. The derivative peptides belong to natural derivative peptides, with high safety, high memory-improving activity, anti-acid-base stability, and gastrointestinal digestion stability. The derivative peptides can be used in the preparation of memory-improving and antioxidant medicaments and health care products, and have an excellent application prospects.

According to a sequence design method of the derivative peptides provided by the present disclosure, the high-activity memory-improving peptide can be obtained without enzymatic hydrolysis, separation and purification, and the design method is simple and rational. The primary structure or spatial conformation of a bioactive peptide is the key to determining functional activity thereof. The rational design and molecular docking simulation screening adopted in the present disclosure are conducive to the directional acquisition of memory-improving active peptides, which are characterized by higher activity, higher stability and higher safety. The memory-improving active peptides can be used to prevent or delay memory impairment and thus delay the pathogenesis and progression of dementia, having great potential for the development of medicaments, health care products and foods and inevitably playing an important role.

BRIEF DESCRIPTION OF THE DRAWINGS

FIG. 1 illustrates the separation, purification and structural identification of a pine nut antioxidant peptide WYPGK (SEQ ID NO: 1)

FIG. 2 illustrates curves of pine nut memory-improving derivative peptides WYPGK (SEQ ID NO: 1) and WYSGK (SEQ ID NO: 4) in Morris water maze for mice.

DETAILED DESCRIPTION OF THE EMBODIMENTS

The present disclosure will be further explained below in conjunction with the examples, but the examples do not limit the present disclosure in any way.

Example 1: Separation, Purification and Structural Identification of a Pine Nut Antioxidant Peptide WYPGK (SEQ ID NO:1)

(1) Preparation of a Pine Nut Antioxidant Peptide

With pine nut albumin as a raw material, distilled water was added to prepare a 2% substrate concentration, and incubated in a water bath at 90° C. for 10 min to destroy the protein structure. After cooling to room temperature, the pH was adjusted to 9.5 with 0.5 mol/L NaOH, and the temperature of enzymatic hydrolysis was set at 57° C. The adding amount of Alcalase 2.4 L was 8,600 U/g, and the enzymatic hydrolysis time was 150 min. The enzyme was inactivated at 90° C. for 10 min after the enzymatic hydrolysis was completed. After cooling to room temperature, the pH was adjusted to 7.0 with 0.5 mol/L HCl; after centrifugation at 5,000 r/min for 10 min, a supernatant was collected to obtain enzymatic hydrolyzate, which was stored at 4° C.

(2) Ultrafiltration

Figure 1A:
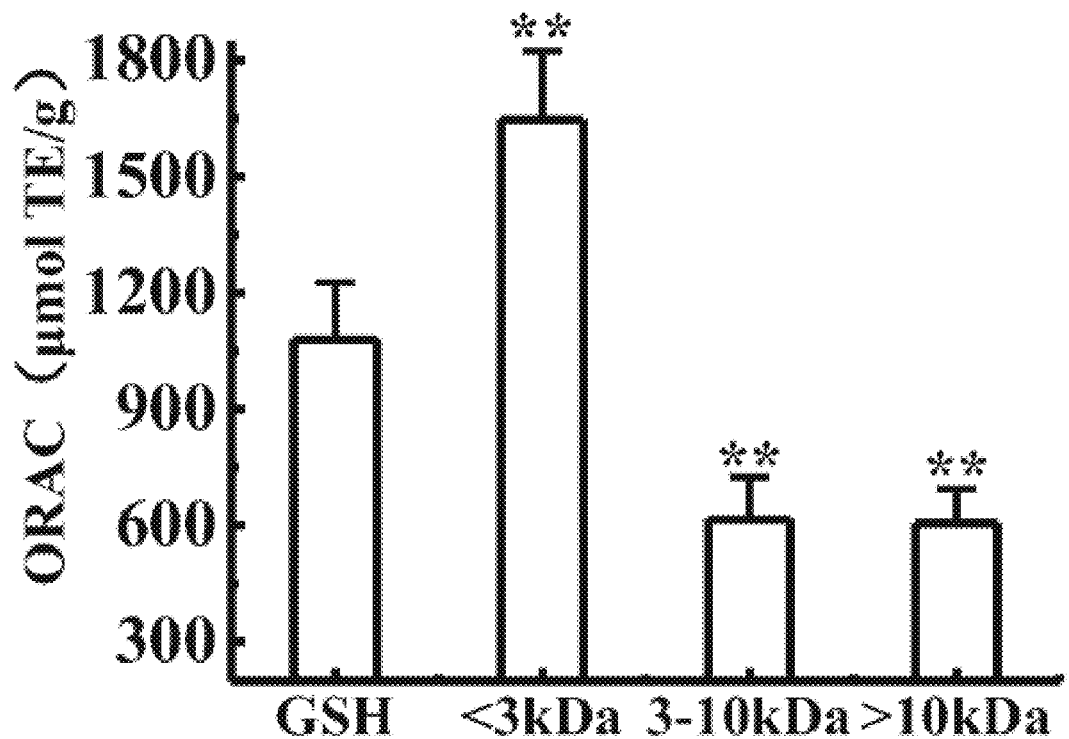
FIG. 1A illustrates the ORAC assay of ultrafiltration fractions.

The enzymatic hydrolyzate of pine nut antioxidant peptide obtained in step (1) was separated by ultrafiltration using a polyethersulfone membrane (Millipore Pellicon XL device; Biomax, cut off 10 kDa and 3 kDa; MA) connected to a tangential flow filtration system (Labscale; Millipore, MA, USA). The molecular weight cutoffs were 10 kDa and 3 kDa, respectively. The inlet pressure of the constant flow pump was controlled at 1.5 bar, and the backflow pressure was 0.4 bar. Three fractions (molecular weights <3 kDa, 3-10 kDa, and >10 kDa) were obtained. The three fractions were collected separately and lyophilized into powders, and their antioxidant activity was determined by ORAC assay (see Example 3 for specific experimental methods). The results showed that the fraction with a molecular weight of <3 kDa in the pine nut antioxidant peptide had better antioxidant activity (see FIG. 1a).

(3) Sephadex G-25 Gel Chromatography

Figure 1B:
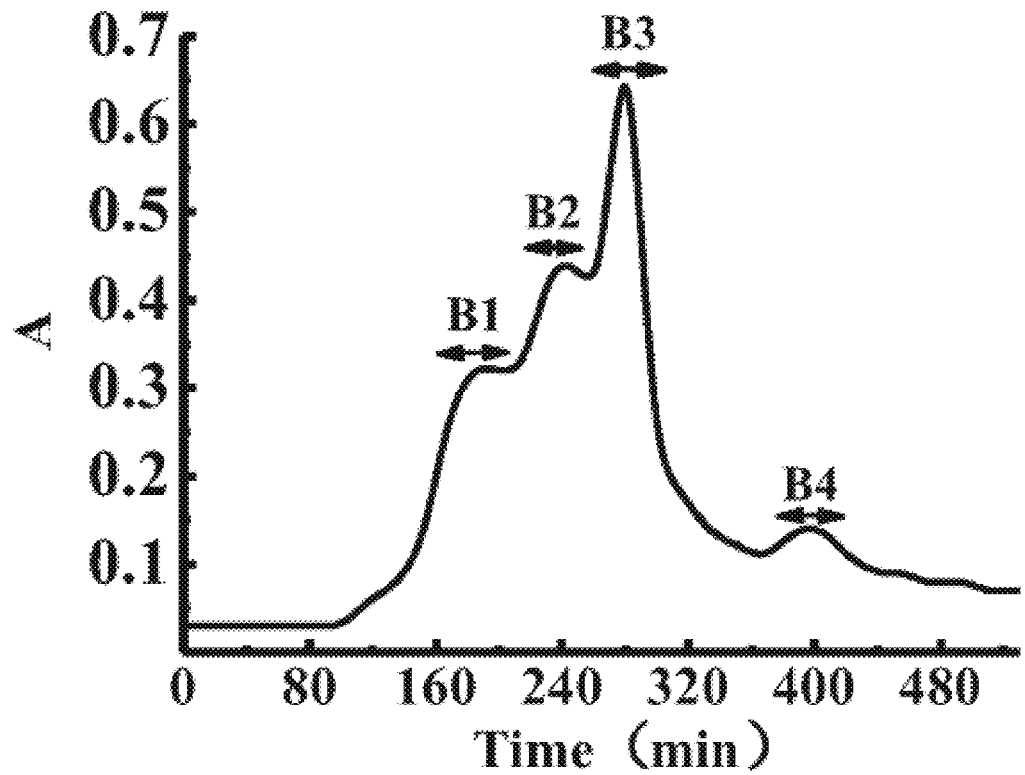
FIG. 1B is a Sephdex G-25 chromatogram.
Figure 1C:
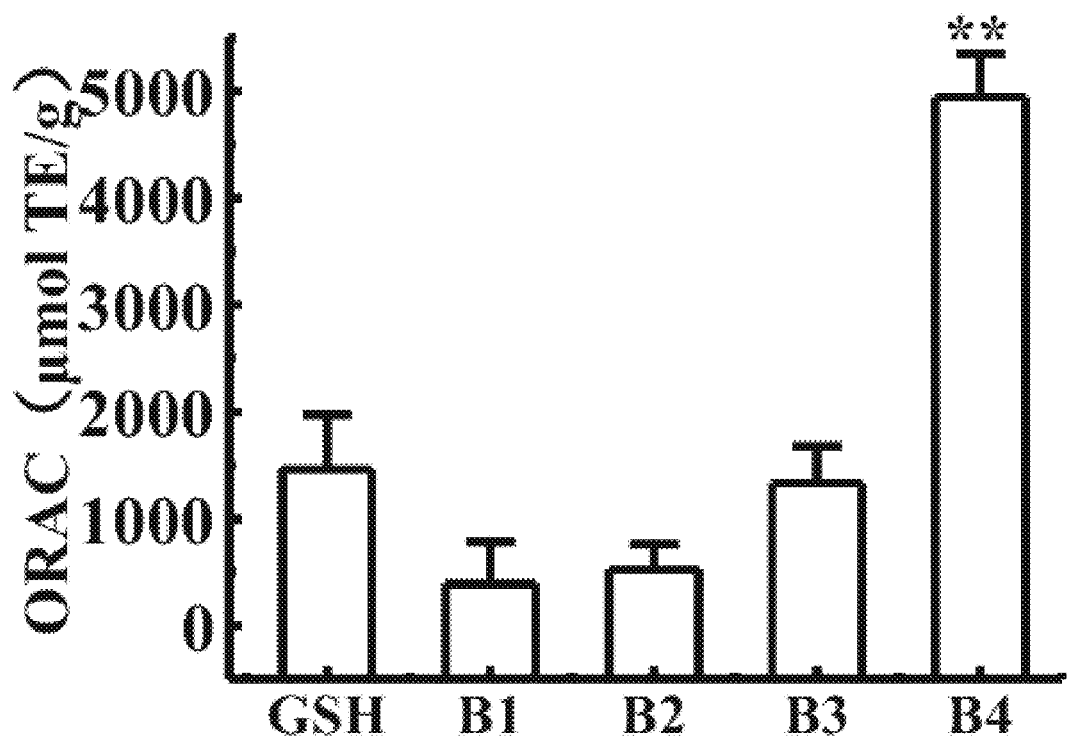
FIG. 1C illustrates the ORAC assay of fractions of Sephdex G-25.

The fraction with a molecular weight of <3 kDa in the pine nut antioxidant peptide obtained in step (2) was dissolved in distilled water to prepare a 100 mg/mL solution, and the solution was filtered through a 0.22 μm filter membrane. The filtrate was separated by Sephadex G-25 Column (1.6×80 cm). The loading sample was 15 mL, the eluent was distilled water, and the elution flow rate was 1.5 mL/min. The absorbance of the sample during the separation was measured at a wavelength of 280 nm using an ultraviolet spectrophotometer, and fractions (5 min/tube) were collected by using an automatic fraction collector. Four fractions (B1, B2, B3, and B4; the four fractions obtained had different molecular weights, and the molecular weights were ranked in descending order) were obtained by chromatography (see FIG. 1B, where A on a vertical axis represents absorbance). The four fractions were collected separately and lyophilized into powders, and their antioxidant activity was determined by ORAC assay. The results showed that the fraction B4 of the pine nut antioxidant peptide has better antioxidant activity (see FIG. 1C).

(4) Sephadex G-15 Gel Chromatography

Figure 1D:
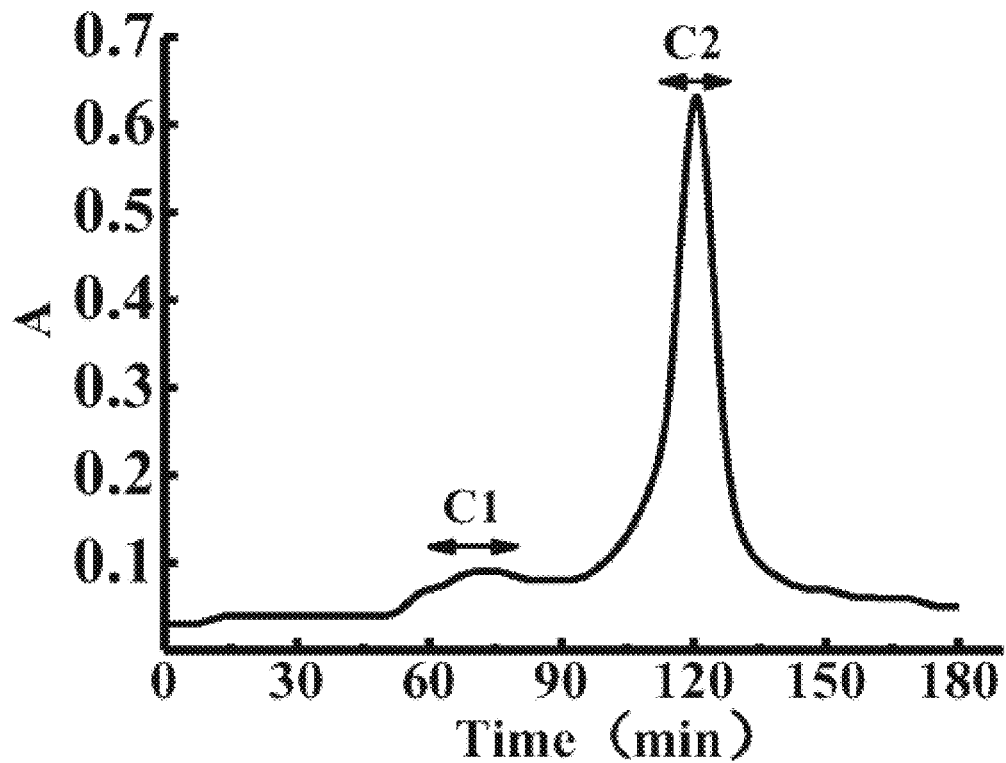
FIG. 1D is a Sephdex G-15 chromatogram.
Figure 1E:
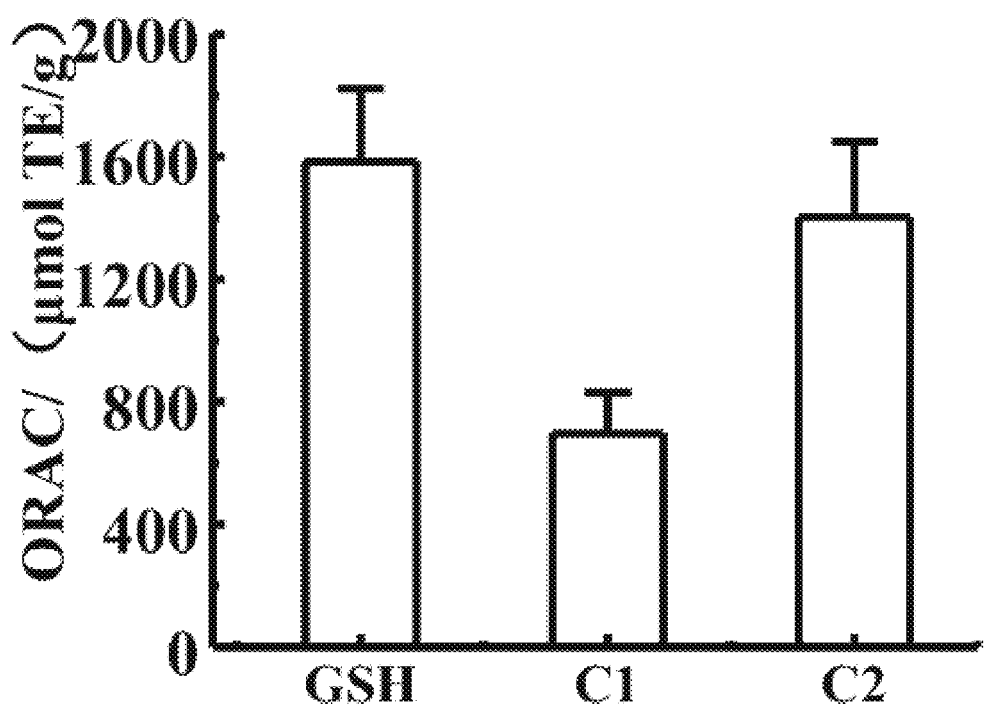
FIG. 1E illustrates the ORAC assay of fractions of Sephdex G-15.

The fraction B4 of the pine nut antioxidant peptide separated by Sephadex G-25 gel chromatography was dissolved in distilled water to prepare an 80 mg/mL solution, and the solution was filtered through a 0.22 μm filter membrane. The filtrate was separated by Sephadex G-15 Column (1.6×80 cm). The loading sample was 1.5 mL, the eluent was distilled water, and the elution flow rate was 0.8 mL/min. The absorbance of the sample during the separation was measured at a wavelength of 280 nm using an ultraviolet spectrophotometer, and fractions (5 min/tube) were collected by using an automatic fraction collector. Two fractions (C1 and C2; the two fractions obtained had different molecular weights, and the molecular weights were ranked in descending order) were obtained by chromatography (see FIG. 1D). The two fractions were collected separately and lyophilized into powders, and their antioxidant activity was determined by ORAC assay. The results showed that the fraction C2 of the pine nut antioxidant peptide has better antioxidant activity (see FIG. 1E).

(5) RP-HPLC

Figure 1F:
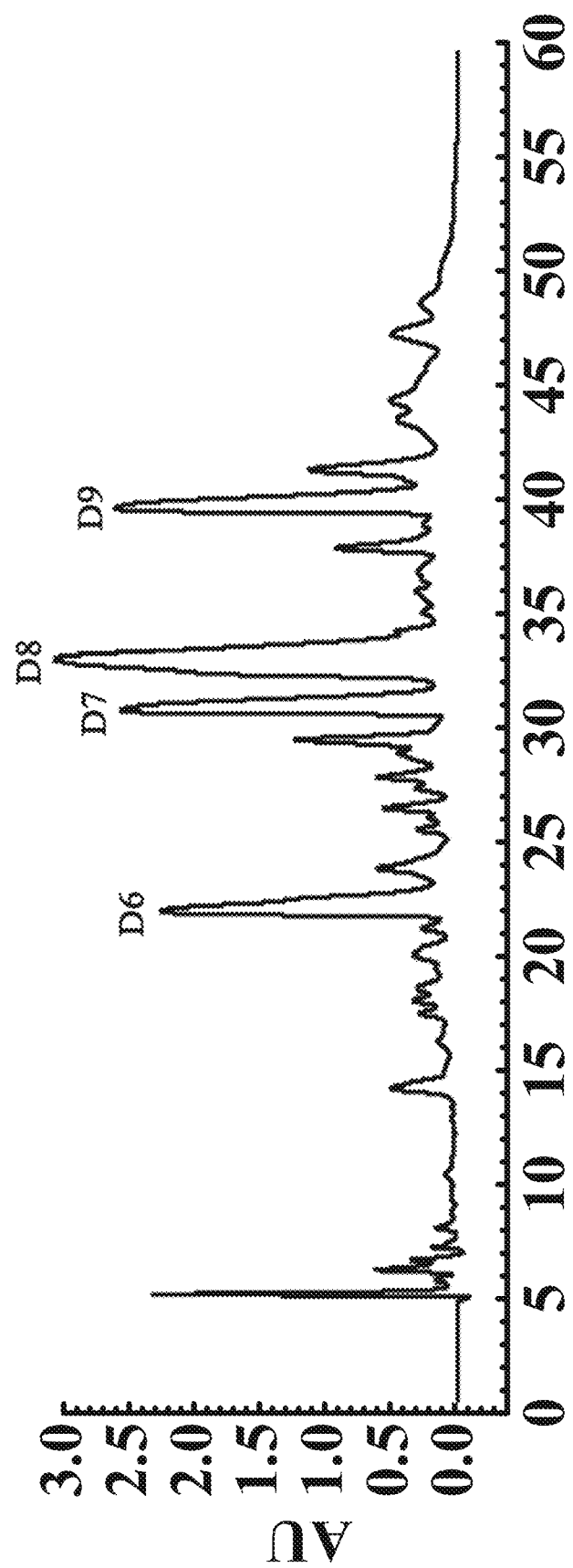
FIG. 1F is a reversed phase high performance liquid chromatography (RP-HPLC) spectrum.
Figure 1G:
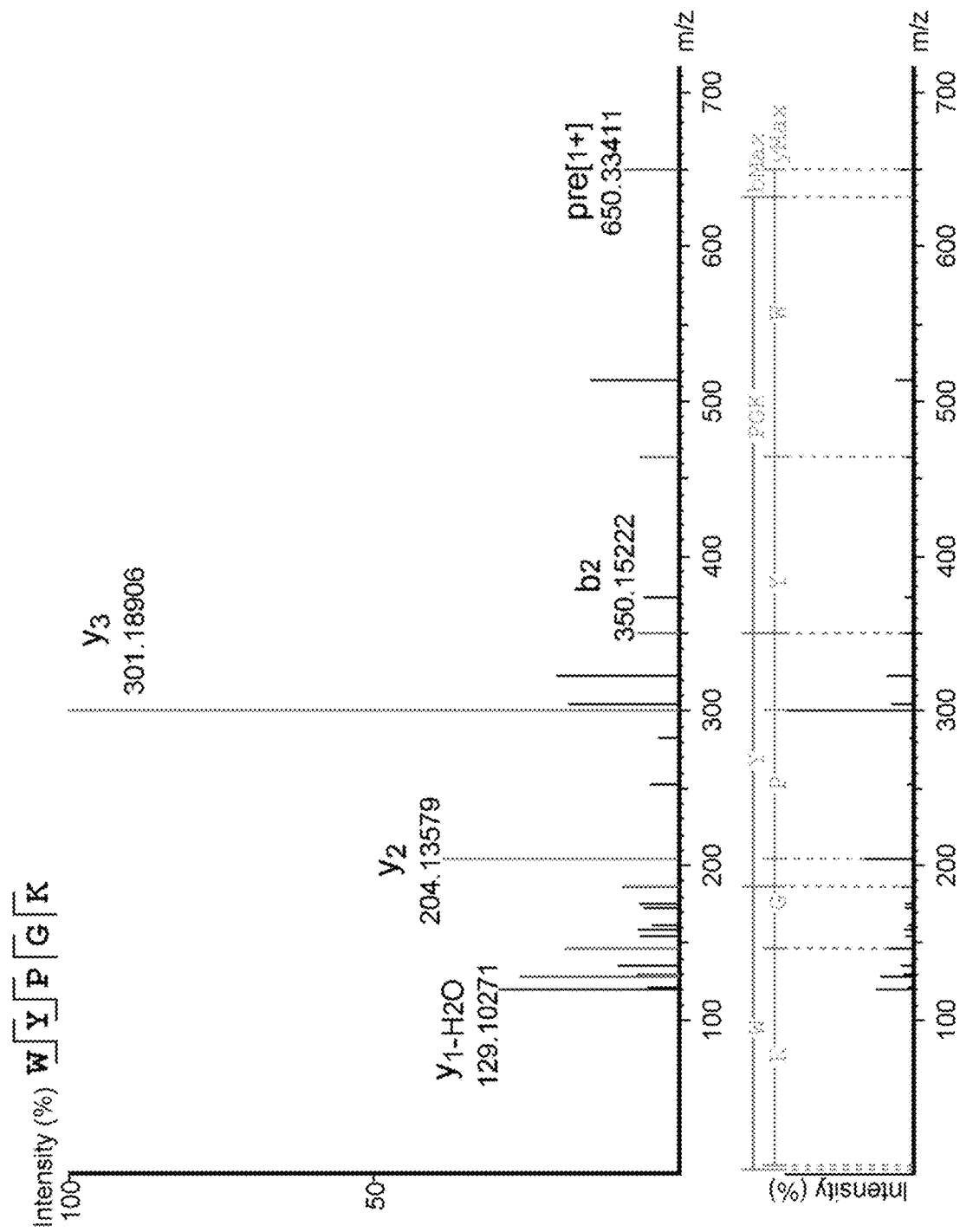
FIG. 1G is a mass spectrum of the pine nut antioxidant peptide WYPGK (SEQ ID NO: 1)

The fraction C2 of the pine nut antioxidant peptide separated by Sephadex G-15 gel chromatography was dissolved in distilled water to prepare a 40 mg/mL sample solution, and the solution was filtered through a 0.22 μm filter membrane. The filtrate was collected and loaded on an RP-HPLC system for separation and purification. Chromatographic conditions were as follows: C18 (4.6×150 mm); detection wavelength: 220 nm; sample injection volume: 50 μL; flow rate: 0.5 mL/min; column temperature: 25° C.; phase A: water+0.1% (v/v) trifluoroacetic acid (TFA); and phase B: methanol+0.1% (v/v) TFA. The elution conditions of liquid phases are shown in Table 1. The separated fractions were collected and lyophilized into powders, and the collected fractions were sampled and sent for mass spectrometry (see FIGS. 1f and 1g; the curve in FIG. 1F is a liquid chromatogram; the AU on the vertical axis represents the absorbance; and high absorbance indicates high content and purity of peptides in the fraction; four fractions, D6 to D9, were collected, the four fractions obtained had different peptide polarities, and the polarities were ranked in descending order).

TABLE 1

| Elution conditions of mobile phases | | |
|---|---|---|
| Time (min) | A (%) | B (%) |
| 0 | 95 | 5 |
| 30 | 70 | 30 |
| 50 | 70 | 30 |
| 60 | 95 | 5 |

(6) Structural Identification of Peptides

Structural identification of peptides was performed by liquid chromatography-electrospray ionization-tandem mass spectrometry (LC-ESI-MS/MS) using the Q Exactive (QE) mass spectrometer (Thermo Fisher Scientific Inc., USA). Positive electrospray ionization mode (ESI$^+$) was used; the mass scan range (m/z) was from 50 to 750; the sheath gas was nitrogen ($N_2$), at a pressure of 40 au; the auxiliary gas was nitrogen ($N_2$) at 5 au; the spray voltage was at 4.5 KV; the capillary temperature was 350° C.; and the collision voltage of the secondary MS was 15 eV. Spectral data were collected, and amino acid sequence analysis was performed by de novo sequencing using PEAKS software. Through database and literature review, peptide fragments identified by MS were screened to obtain a pine nut antioxidant peptide WYPGK (SEQ ID NO:1, see FIG. 1G).

Example 2: Improvement of the Learning and Memory of Scopolamine-Induced Memory Impairment Model Mice by High-Activity Memory-Improving Derivative Peptides The Proline of the pine nut antioxidant peptide WYPGK (SEQ ID NO: 1) was substituted with 19 common amino acids (glycine G, alanine A, valine V, leucine L, isoleucine I, methionine M, tryptophan W, serine S, lysineK, cysteine C, phenylalanine F, asparagine N, glutamine Q, threonine T, aspartate D, glutamate E, tyrosine Y, arginine R, and histidine H) to obtain sequences of 19 derivative peptides (WYGGK (SEQ ID NO: 6), WYAGK (SEQ ID NO: 7), WYVGK (SEQ ID NO: 8), WYLGK (SEQ ID NO: 9), WYIGK (SEQ ID NO: 10), WYMGK (SEQ ID NO: 11), WYWGK (SEQ ID NO: 12), WYSGK (SEQ ID NO: 4), WYKGK (SEQ ID NO: 3), WYCGK (SEQ ID NO: 13), WYFGK (SEQ ID NO: 5), WYNGK (SEQ ID NO: 14), WYQGK (SEQ ID NO: 15), WYTGK (SEQ ID NO: 16), WYDGK (SEQ ID NO: 17), WYEGK (SEQ ID NO: 2), WYYGK (SEQ ID NO: 18), WYRGK (SEQ ID NO: 19), and WYHGK (SEQ ID NO: 20)); the 19 derivative peptides could be directly synthesized by the company), respectively. The 19 derivative peptides were subjected to molecular docking with mitochondrial NAD+-dependent deacetylase sirtuin 3 (SIRT3) and screened by the binding energy. It was determined that the binding energy of the derivative peptide WYSGK (SEQ ID NO: 4), WYEGK (SEQ ID NO: 2), WYKGK (SEQ ID NO:3), WYFGK (SEQ ID NO: 5) was −5.87, −1.44, −1.94, −6.08, respectively. WYEGK (SEQ ID NO: 2), WYKGK (SEQ ID NO: 3), WYSGK (SEQ ID NO: 4), WYFGK (SEQ ID NO: 5), and WYPGK (SEQ ID NO: 1) were subjected to solid-phase chemical synthesis (refer to the method by Sheppard R., J. Pept. Sci. 2003; 9:545.) to obtain five peptides, and the memory-improving activity analysis was conducted on scopolamine-induced memory impairment model mice.

In vivo studies were performed in accordance with the *Guide for the Care and Use of Laboratory Animals* published by the European Commission. Male C57BL/6N mice weighing 25-30 g were purchased from Liaoning Changsheng Biotechnology Co., Ltd. (Benxi, China). Mice were housed at a stable temperature (22±1° C.) under a 12 h/12 h light/dark cycle. The mice were given access to standard diet and water ad libitum. The mice were divided into five groups (n=10/group): (i) mice administered by gavage with saline as vehicle for 36 days (control); (ii) mice administered by gavage with saline for 30 days and scopolamine (1 mg/kg) for 6 days (model); (iii) mice administered by gavage with saline for 30 days and piracetam (60 mg/kg) and scopolamine (1 mg/kg) for 6 days (positive); (iv) mice administered by gavage with the fraction of <3 kDa (600 mg/kg) for 30 days and the fraction of <3 kDa (600 mg/kg) and scopolamine (1 mg/kg) for 6 days (<3 kDa); and (v) mice administered by gavage with peptide WYPGK (SEQ ID NO: 1, 60 mg/kg) for 30 days and peptides WYPGK (SEQ ID NO: 1, 60 mg/kg) and scopolamine (1 mg/kg) for 6 days (WYPGK, SEQ ID NO: 1).

Morris Water Maze (1) Place Navigation

Figure 2A:
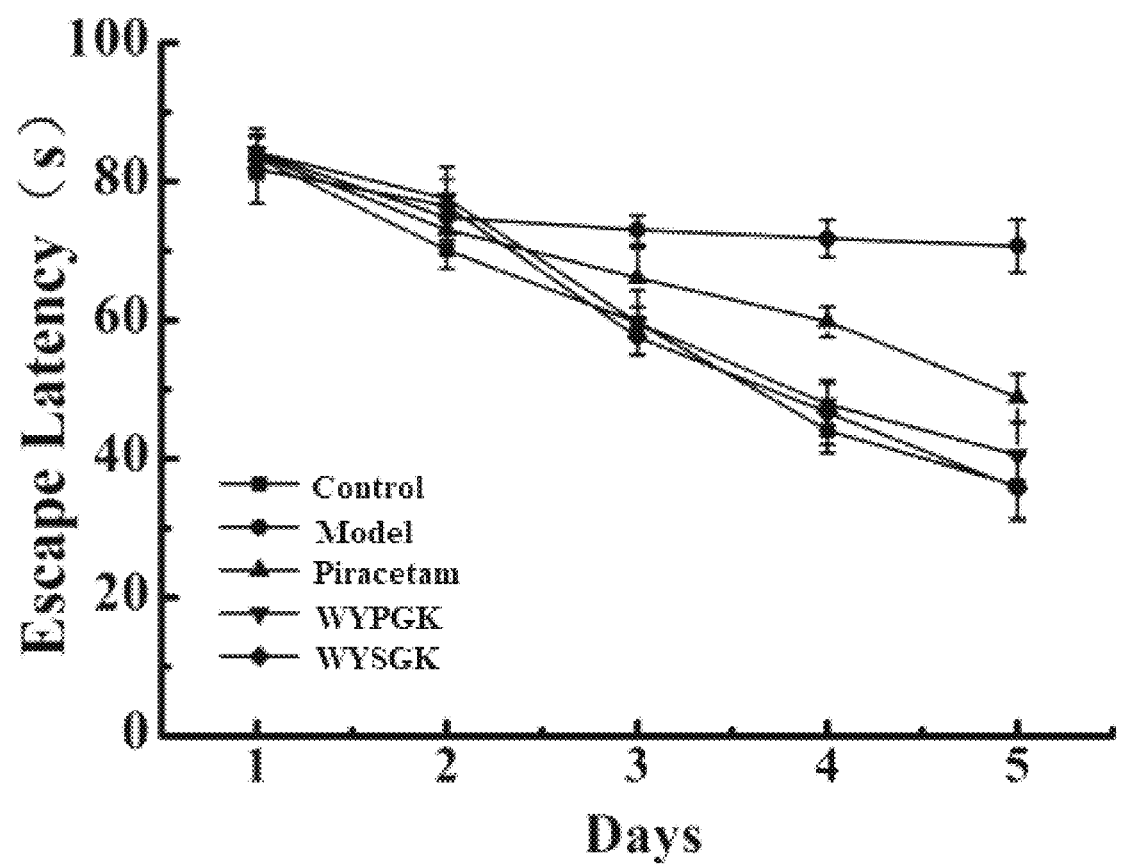
FIG. 2A shows escape latency curves.

A circular pool for Morris water maze (1,200 mm in diameter) was filled with warm water at 20±2° C., while a platform (65 mm diameter) was hidden in the Southwest (SW) quadrant 1 cm below the water surface. A mouse was gently placed in the Northeast (NE) quadrant facing the pool wall, the swimming trajectory of the mouse was recorded by the image acquisition system, and the time was measured for 120 s. The time it took to find the platform in the SW quadrant within 120 s was recorded as the latency, while the mouse that reached the platform was allowed to sit on the platform for 10 s and then returned to the holding cage. Mice that failed to find the platform within 120 s were guided onto the platform and were also allowed to sit on the platform for 10 s, and the latency was recorded as 120 s. Subsequently, the time from the mice being placed in the water to finding the platform was analyzed and calculated according to the data acquisition system (see FIG. 2A). As shown in FIG. 2A, during the 5-day training, compared with the control group, the mice of the model group (Model) had longer escape latency, indicating that the mice of the model group had memory impairment; compared with the model group, the mice of the derivative peptides WYPGK (SEQ ID NO: 1) and WYSGK (SEQ ID NO: 4) groups showed shorter escape latency, and the short latency indicated that the mice had good memory. Therefore, memory impairment was alleviated in the mice of the derivative peptides WYPGK (SEQ ID NO: 1) and WYSGK (SEQ ID NO: 4) groups, and the derivative peptides WYPGK (SEQ ID NO: 1) and WYSGK (SEQ ID NO: 4) played a role in improving the learning and memory of the scopolamine-induced memory impairment model mice.

(2) Probe Trial

Figure 2B:
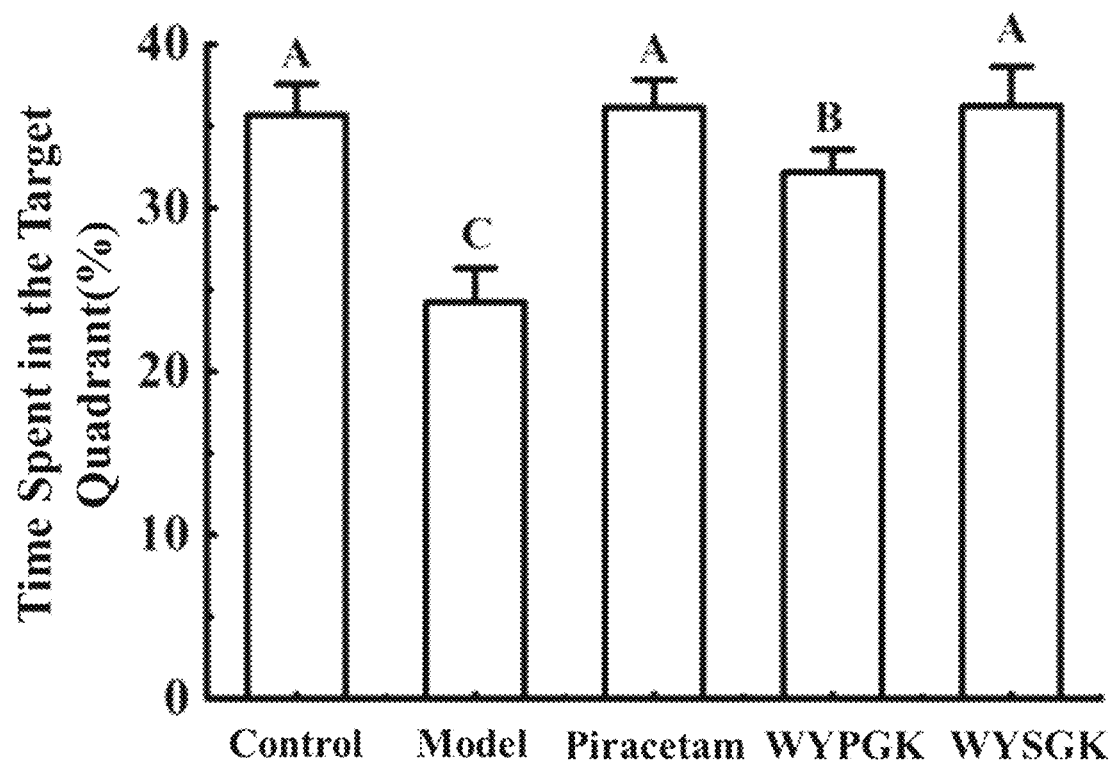
FIG. 2B shows a histogram of percent time spent in target quadrant.
Figure 2C:
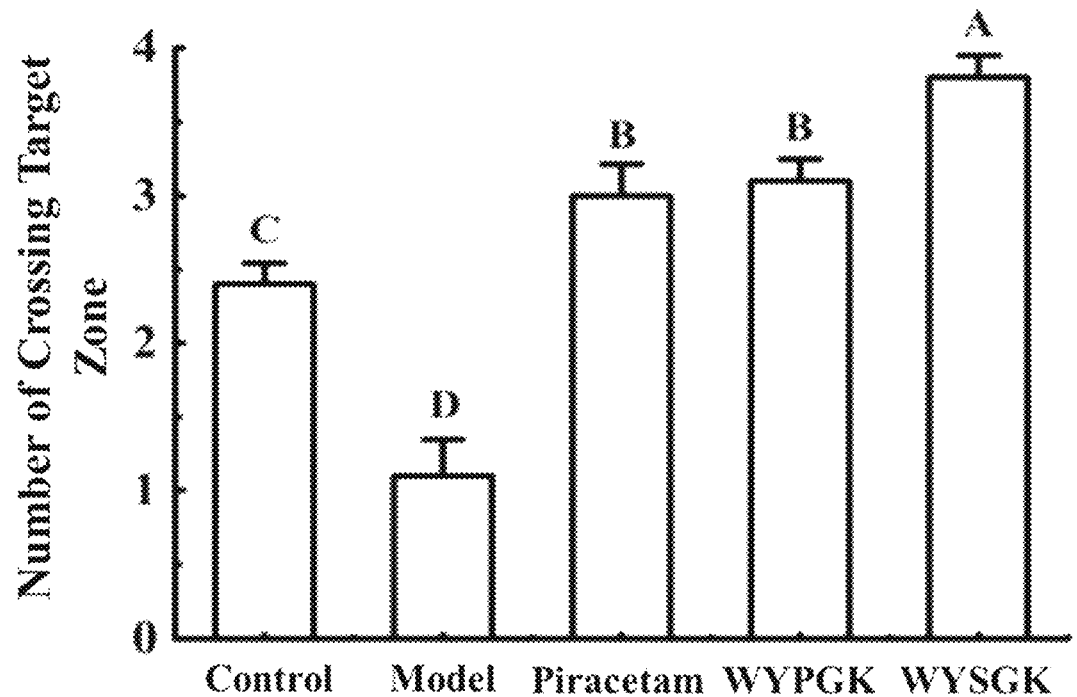
FIG. 2C shows a histogram of the frequency of platform crossing, where Model group represents scopolamine impaired group, and Piracetam represents a positive group.

After the place navigation was completed, the platform hidden in the water was taken out. A mouse was gently placed in the Northeast (NE) quadrant facing the pool wall, the swimming trajectory of the mouse was recorded by the image acquisition system, and the time was measured for 90 s. According to the data acquisition system, the time spent in the target quadrant (see FIG. 2B) and the frequency of original platform crossing (see FIG. 2C) within 90 s were analyzed and calculated on the mouse. As shown in FIGS. 2b and 2c, compared with the blank group (Control), the mice of the model group (Model) showed significant decreases in the time spent in target quadrant and the frequency of original platform crossing, indicating that the mice of the model group had memory impairment; compared with the model group, the mice of the derivative peptides WYPGK (SEQ ID NO: 1) and WYSGK (SEQ ID NO: 4) groups showed significant decreases in the time spent in target quadrant and the frequency of original platform crossing, indicating that memory impairment was alleviated in the mice of the derivative peptides WYPGK (SEQ ID NO: 1) and WYSGK (SEQ ID NO: 4) groups. The derivative peptides WYPGK (SEQ ID NO: 1) and WYSGK (SEQ ID NO: 4) played a role in improving the learning and memory of the scopolamine-induced memory impairment model mice.

Example 3: Determination of the Antioxidant Activity of Derivative Peptides from Pine Nut Antioxidant Peptide (see FIG. 3)

(1) ABTS free radical scavenging assay: Equal volumes of a 7 mmol/L ABTS aqueous solution and a 2.49 mmol/L potassium persulfate aqueous solution were mixed and left to stand in the dark for 12 h to obtain an ABTS free radical stock solution, which was stored at 4° C. When in use, the stock solution was diluted with 5 mmol/L PBS until the absorbance of the solution was 0.700±0.002 at 734 nm, and an ABTS free radical working solution was prepared. Separately, 10 μL of each of the aqueous solutions of derivative peptides with a concentration of 100 μM was added to a 96-well plate, while glutathione (GSH) of the same concentration was used as a control; these solutions reacted with 190 μL of ABTS free radical working solution accurately for 6 min, and absorbance values ($A_1$) were measured at a wavelength of 734 nm using a microplate reader. The calculation formula for scavenging rate is as follows:

$$\text{Scavenging rate } \% = \frac{A_0 - (A_1 - A_2)}{A_0} \times 100\%$$

where $A_0$ is the absorbance value that replaces the derivative peptide solution with distilled water;

$A_1$ is the absorbance value of the solution adding a derivative peptide or GSH; and $A_2$ is the absorbance value of the solution using 5 mmol/L PBS instead of the ABTS free radical working solution.

(2) ORAC assay: (1) On a 96-well black plate, 25 μL each of PBS, Trolox standard solutions (12.5, 25, 50, and 100 μM) and aqueous solutions of five derivative peptides (100 μM) was added. The 96-well plate was placed and shaken in a microplate reader preheated for 30 min for 5 s, and incubated at 37° C. for 10 min. To each well, 150 μL each of FL working solution was added using a multi-channel pipette, and the plate was shaken for 5 s and incubated at 37° C. for 20 min. To each well, 25 μL each of AAPH was quickly added using the multi-channel pipette, and the plate was shaken for 5 s, followed by reading. The fluorescence intensity was continuously measured at an excitation wavelength of (485±20) nm and an emission wavelength of (530±20) nm. The whole system was held at 37° C., and the fluorescence intensity was measured every 2 min. Before each measurement, the well plate was shaken at a medium speed for 10 s, and the oscillation amplitude was 4 mm. The measurement was performed until the fluorescence intensity reached 5% of the initial fluorescence intensity (60 cycles were set in this assay). The relative fluorescence intensity is calculated by the area under the fluorescence decay curve (AUC) as follows:

$$AUC=0.5\times[2\times(f_0+f_1 \ldots +f_{n-1}+f_n)-f_0-f_n]\times\Delta t$$

(1) In the formula, $f_n$ is the relative fluorescence intensity at the n-th measurement point; and $\Delta t$ is the interval between adjacent time points, namely 2 min.

(2) The measurement results are expressed as ORAC values. The ORAC values of unknown samples are expressed in μmol TE/g.

$$ORAC\ value=[(AUC_{Sample}-AUC_{Blank})/(AUC_{Trolox}-AUC_{Blank})]\times C_{Trolox}/C_{Sample}.$$

Herein, $AUC_{Sample}$ is the result of each of the aqueous solutions of five derivative peptides; $AUC_{Blank}$ is the result after adding 25 μL of PBS; $AUC_{Trolox}$ is the result after adding Trolox standard solution (100 μM); $C_{Trolox}$ is the molar concentration of Trolox, namely, 100 μM;

$C_{Sample}$ is the molar concentration of each derivative peptide, calculated from the Trolox standard curve, where the Trolox standard curve is y=0.0756x+41.989, $R^2$=0.9931, the abscissa is the molar concentration of Trolox (12.5, 25, 50, or 100 μM), and the ordinate is $AUC_{Trolox}$.

Figure 3:
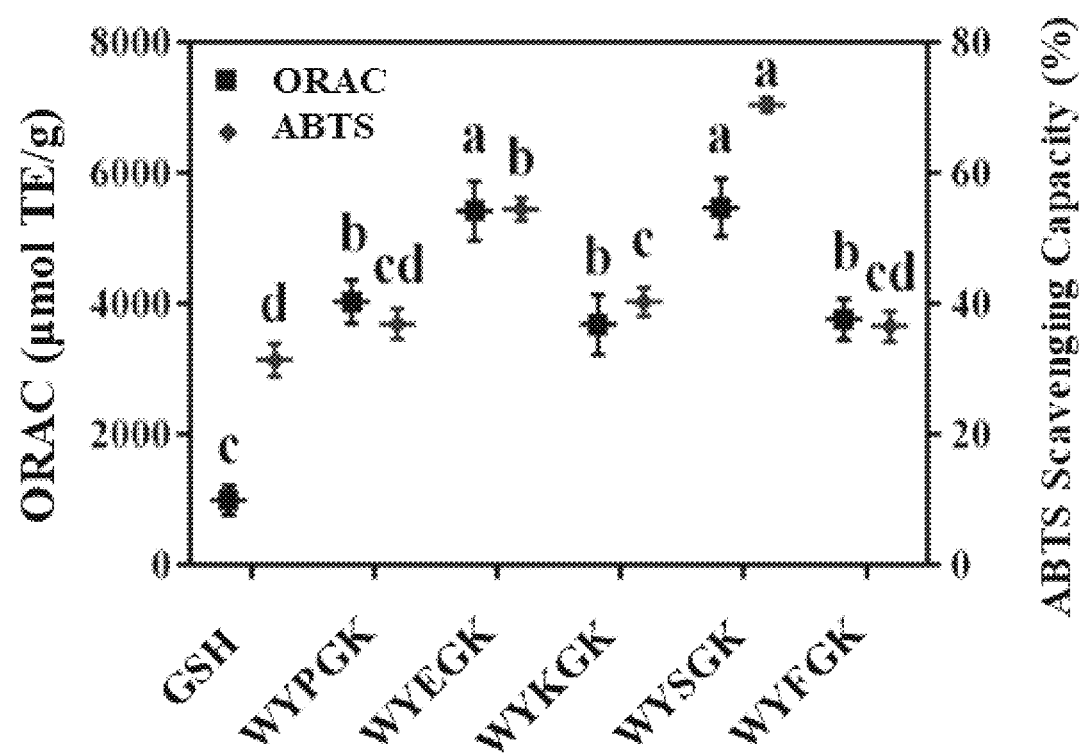
FIG. 3 illustrates curves of ABTS free radical scavenging and ORAC assays of a pine nut antioxidant peptide WYPGK (SEQ ID NO: 1) and pine nut memory-improving derivative peptides WYEGK (SEQ ID NO: 2), WYKGK (SEQ ID NO: 3), WYSGK (SEQ ID NO: 4), and WYFGK (SEQ ID NO: 5)

As shown in FIG. 3, in the free radical scavenging assay, the right ordinate is the ABTS free radical scavenging rate. Compared with the positive control GSH, the ABTS free radical scavenging rate of the derivative peptides WYEGK (SEQ ID NO: 2), WYKGK (SEQ ID NO: 3), WYSGK (SEQ ID NO: 4), and WYFGK (SEQ ID NO: 5) reached 54.48%, 40.31%, 70.47%, and 36.56%, respectively, all of which were higher than the GSH (31.39%). In the ORAC assay, the left ordinate is the ORAC, and the ORAC values of the derivative peptides WYEGK (SEQ ID NO: 2), WYKGK (SEQ ID NO: 3), WYSGK (SEQ ID NO: 4), and WYFGK (SEQ ID NO: 5) reached 5,422.29, 3,681.50, 5,473.16, and 3,762.05 μmol TE/g, respectively, all of which were significantly higher than the GSH (995.58 μmol TE/g), indicating that the high-activity memory-improving derivative peptide provided by the present disclosure had high antioxidant activity.

Figure 4A:
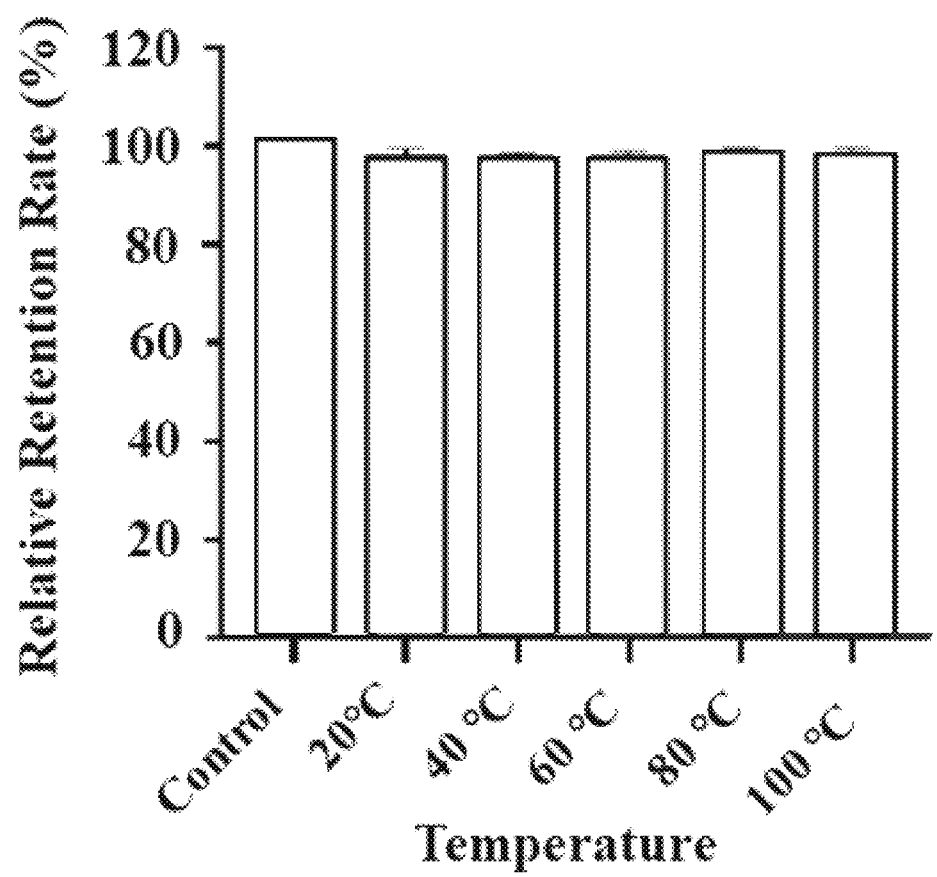
FIG. 4 illustrates the temperature stability (a) and acid-base stability (b) of a pine nut memory-improving derivative peptide WYSGK (SEQ ID NO: 4)

Example 4: Stability Testing of Derivative Peptides of the Pine Nut Antioxidant Peptide For peptide stability testing, the specific experimental procedure was as follows:

Thermal Stability Testing (see FIG. 4A):

Step 1, the solid powder of derivative peptide WYSGK (SEQ ID NO:4) was dissolved in distilled water to prepare a 100 μM solution, the pH value was adjusted to 7.0, and the resulting solution was stored at 4° C. for later use;

Step 2, the derivative peptide WYSGK (SEQ ID NO: 4) solution in step 1 was divided into five tubes (1 mL/tube), and each tube was placed in a water bath at 20, 40, 60, 80, and 100° C. for 2 h;

Step 3, the blank group (the derivative peptide WYSGK (SEQ ID NO: 4) solution in step 1 without water bath treatment) and the derivative peptide WYSGK (SEQ ID NO:4) solution at each temperature were filtered through a 0.22 μm filter membrane;

Step 4, RP-HPLC was performed under the following conditions: detection wavelength: 220 nm; column temperature: 25° C.; mobile phase A: acetonitrile+0.1% (v/v) TFA; mobile phase B: acetonitrile+0.1% (v/v) TFA. Elution conditions were programmed as follows: 0-25 min, 10%-35% B (the value could be input in the liquid phase equipment); flow rate 1.0 mL/min; and Step 5, the peak area in the liquid chromatogram was calculated to determine whether the derivative peptide WYSGK (SEQ ID NO:4) was degraded at different temperatures (refer to Liu Xintong's method, Sci. Technol. Food Ind., Vol. 41, No. 19, 2020).

Figure 4B:
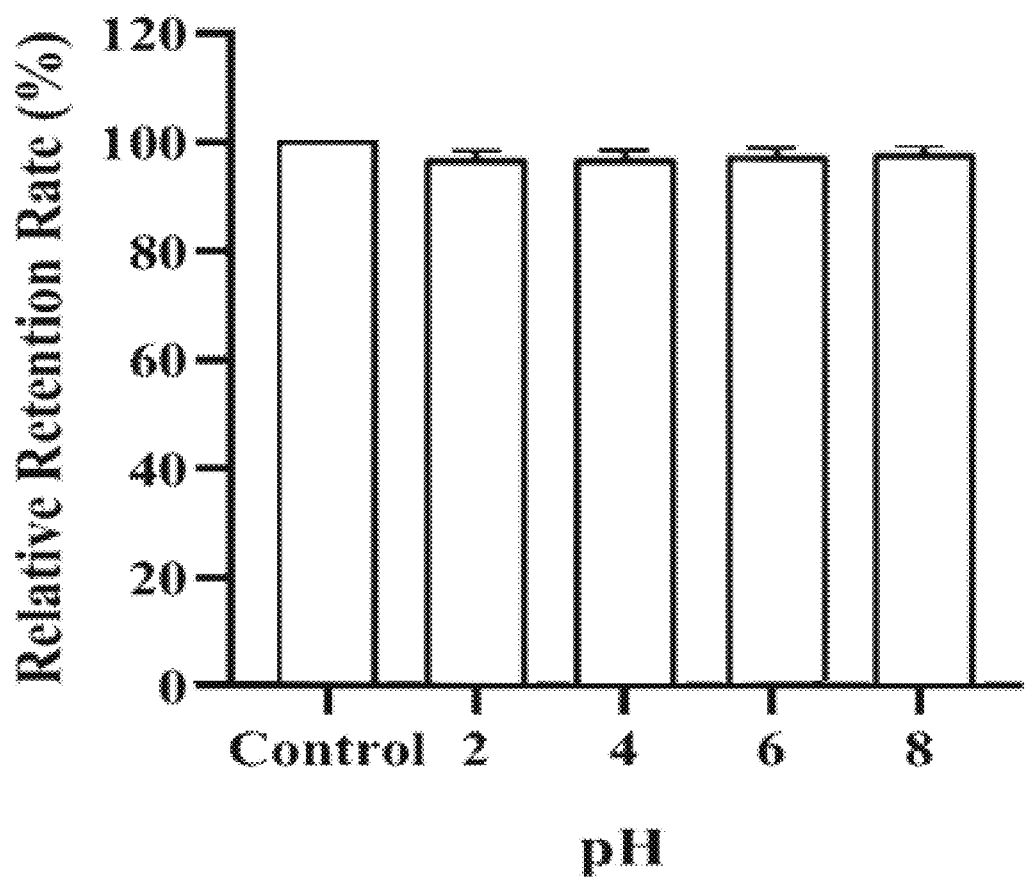

Acid-base Stability Testing (see FIG. 4B):

Step 1, the solid powder of derivative peptide WYSGK (SEQ ID NO: 4) was dissolved in distilled water to prepare a 100 μM solution, which was used as a blank group and stored at 4° C. for later use;

Step 2, the solid powder of derivative peptide WYSGK (SEQ ID NO: 4) was diluted with aqueous solutions with pH 2, 4, 6, and 8 to a concentration of 100 μmol/L, respectively, and the resulting solutions were incubated in a water bath at 37° C. for 2 h;

Step 3, the blank group and WYSGK (SEQ ID NO: 4) sample solutions at different pH were filtered through a 0.22 μm filter membrane;

Step 4, RP-HPLC was performed under the following conditions: detection wavelength: 220 nm; column temperature: 25° C.; mobile phase A: 100% acetonitrile+0.1% TFA; mobile phase B: 100% acetonitrile+0.1% TFA. Elution conditions were programmed as follows: 0-25 min, 10%-35% B (gradient elution); flow rate 1.0 mL/min; and Step 5, the peak area in the liquid chromatogram was calculated to determine whether the derivative peptide WYSGK (SEQ ID NO: 4) was degraded at different pH (refer to Liu Xintong's method, Sci. Technol. Food Ind., Vol. 41, No. 19, 2020).

As shown in FIG. 4, through experimental analyses of thermal stability and acid-base stability, the derivative peptides were hardly degraded at 20-100° C. and under the acid-base conditions (at pH 2, 4, 6, and 8), indicating that the derivative peptide WYSGK (SEQ ID NO:4) had excellent stability.

Simulated gastrointestinal digestion stability testing of peptides (see FIG. 5):

Step 1, the solid powder of the derivative peptide WYSGK (SEQ ID NO: 4) was dissolved in an aqueous solution with a pH value of 2 to obtain a 100 μM solution;

Step 2, 5 mg of pepsin (enzyme activity was 1:3,000) was added per 1 mL of the derivative peptide solution, 1 mL of the sample was taken for the first time 1 h after incubation in a water bath at 37° C., the digestion of the derivative peptide in the gastric juice was simulated for 1 h, and the resulting enzymatic hydrolyzate was left to stand at 4° C. for use; the enzymatic hydrolyzate was continuously incubated in the water bath at 37° C. for 1 h, 1 mL of the sample was taken for the second time, the digestion of the derivative peptide in the gastric juice was simulated for 2 h, and the resulting enzymatic hydrolyzate was left to stand at 4° C. for later use; the remaining enzymatic hydrolyzate of pepsin was adjusted to pH 7, 5 mg of trypsin was added per 1 mL of the derivative peptide solution (enzyme activity was 1:250) and continuously incubated in the water bath at 37° C.; after 1 h, 1 mL of the sample was taken for the third time, the intestinal digestion of the derivative peptide was simulated for 1 h, and the resulting enzymatic hydrolyzate was left to stand at 4° C. for later use; the enzymatic hydrolyzate was continuously incubated in the water bath at 37° C. for 1 h, 1 mL of the sample was taken for the fourth time, the intestinal digestion of the derivative peptide was simulated for 2 h, and the resulting enzymatic hydrolyzate was left to stand at 4° C. for later use;

after 2 h, the sample was taken out and incubated in the water bath at 37° C. for 2 h; samples were taken every 1 h and left to stand at 4° C. for later use;

Step 3, WYSGK (SEQ ID NO: 4) sample solutions set aside in step 2 were filtered through a 0.22 μm filter membrane, respectively;

Step 4, RP-HPLC was performed under the following conditions: detection wavelength: 220 nm; column temperature: 25° C.; mobile phase A: 100% acetonitrile+0.1% TFA; mobile phase B: 100% acetonitrile+0.1% TFA. Elution conditions were programmed as follows: 0-25 min, 10%-35% B (gradient elution); flow rate 1.0 mL/min; and Step 5, the peak area in the liquid chromatogram was calculated to determine whether the derivative peptide WYSGK (SEQ ID NO:4) was degraded after enzymatic hydrolysis in the presence of pepsin and trypsin (refer to Liu Xintong's method, Sci. Technol. Food Ind., Vol. 41, No. 19, 2020).

Figure 5:
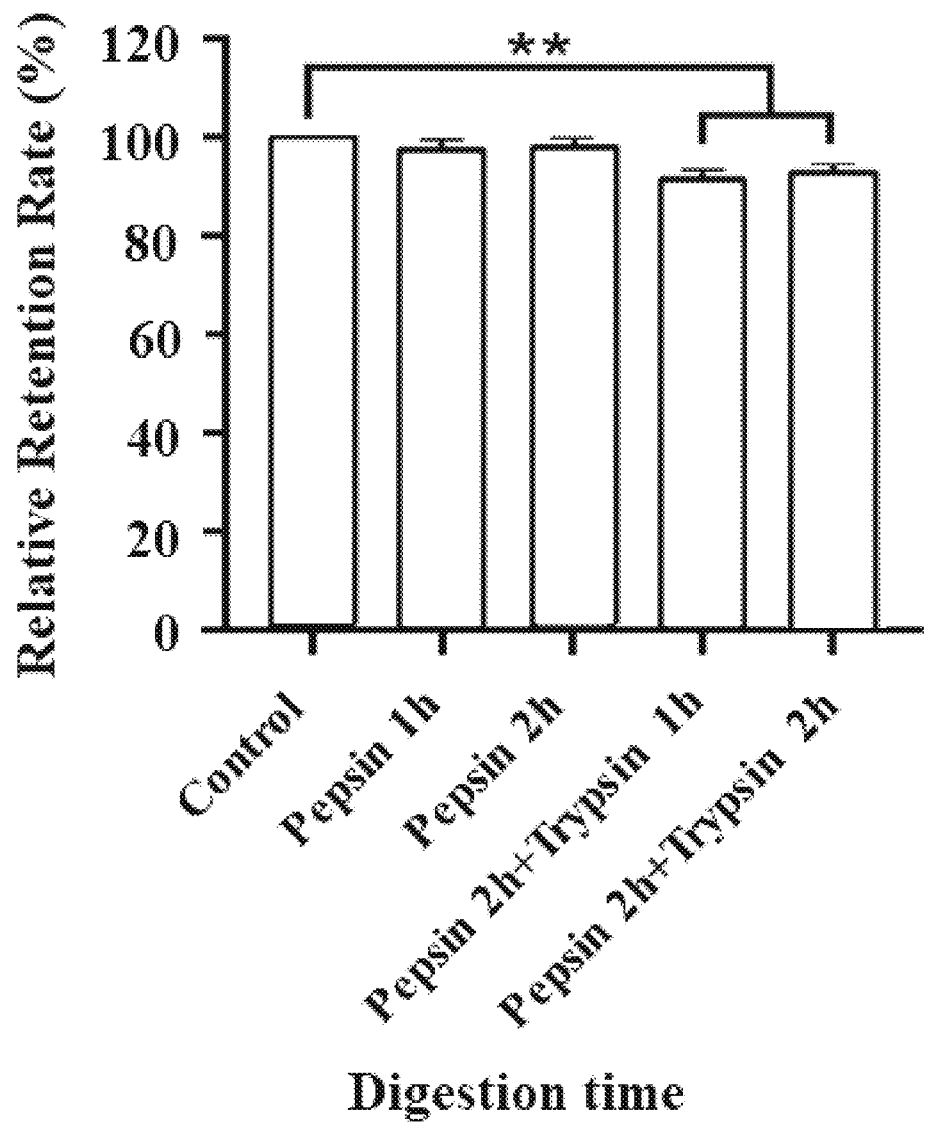
FIG. 5 illustrates the simulated gastrointestinal digestion stability of a pine nut memory-improving derivative peptide WYSGK (SEQ ID NO: 4), where Control represents a blank group without gastrointestinal digestion, Pepsin 1 h represents digestion with pepsin for 1 h, Pepsin 2 h represents digestion with pepsin for 2 h, Pepsin 2 h+Trypsin 1 h represents digestion with pepsin for 2 h and then trypsin for 1 h, and Pepsin 2 h+Trypsin 2 h represents digestion with pepsin for 2 h and then trypsin for 2 h.

As shown in FIG. 5, through the analysis of simulated gastrointestinal digestion experiments, in the presence of pepsin and trypsin, the retention rate of the derivative peptide WYSGK (SEQ ID NO: 4) content reached at least 93.45%, which had excellent gastrointestinal digestion stability.

SEQUENCE LISTING

```
Sequence total quantity: 20
SEQ ID NO: 1              moltype = AA  length = 5
FEATURE                   Location/Qualifiers
source                    1..5
                          mol_type = protein
                          note = pine nut antioxidant peptide
                          organism = synthetic construct
SEQUENCE: 1
WYPGK                                                                  5

SEQ ID NO: 2              moltype = AA  length = 5
FEATURE                   Location/Qualifiers
source                    1..5
                          mol_type = protein
                          note = derivative peptide
                          organism = synthetic construct
SEQUENCE: 2
WYEGK                                                                  5

SEQ ID NO: 3              moltype = AA  length = 5
FEATURE                   Location/Qualifiers
source                    1..5
                          mol_type = protein
                          note = derivative peptide
                          organism = synthetic construct
SEQUENCE: 3
WYKGK                                                                  5

SEQ ID NO: 4              moltype = AA  length = 5
FEATURE                   Location/Qualifiers
source                    1..5
                          mol_type = protein
                          note = derivative peptide
                          organism = synthetic construct
SEQUENCE: 4
WYSGK                                                                  5

SEQ ID NO: 5              moltype = AA  length = 5
FEATURE                   Location/Qualifiers
source                    1..5
                          mol_type = protein
                          note = derivative peptide
                          organism = synthetic construct
SEQUENCE: 5
WYFGK                                                                  5
```

-continued

```
SEQ ID NO: 6       moltype = AA   length = 5
FEATURE            Location/Qualifiers
source             1..5
                   mol_type = protein
                   note = derivative peptide
                   organism = synthetic construct
SEQUENCE: 6
WYGGK                                                                    5

SEQ ID NO: 7       moltype = AA   length = 5
FEATURE            Location/Qualifiers
source             1..5
                   mol_type = protein
                   note = derivative peptide
                   organism = synthetic construct
SEQUENCE: 7
WYAGK                                                                    5

SEQ ID NO: 8       moltype = AA   length = 5
FEATURE            Location/Qualifiers
source             1..5
                   mol_type = protein
                   note = derivative peptide
                   organism = synthetic construct
SEQUENCE: 8
WYVGK                                                                    5

SEQ ID NO: 9       moltype = AA   length = 5
FEATURE            Location/Qualifiers
source             1..5
                   mol_type = protein
                   note = derivative peptide
                   organism = synthetic construct
SEQUENCE: 9
WYLGK                                                                    5

SEQ ID NO: 10      moltype = AA   length = 5
FEATURE            Location/Qualifiers
source             1..5
                   mol_type = protein
                   note = derivative peptide
                   organism = synthetic construct
SEQUENCE: 10
WYIGK                                                                    5

SEQ ID NO: 11      moltype = AA   length = 5
FEATURE            Location/Qualifiers
source             1..5
                   mol_type = protein
                   note = derivative peptide
                   organism = synthetic construct
SEQUENCE: 11
WYMGK                                                                    5

SEQ ID NO: 12      moltype = AA   length = 5
FEATURE            Location/Qualifiers
source             1..5
                   mol_type = protein
                   note = derivative peptide
                   organism = synthetic construct
SEQUENCE: 12
WYWGK                                                                    5

SEQ ID NO: 13      moltype = AA   length = 5
FEATURE            Location/Qualifiers
source             1..5
                   mol_type = protein
                   note = derivative peptide
                   organism = synthetic construct
SEQUENCE: 13
WYCGK                                                                    5

SEQ ID NO: 14      moltype = AA   length = 5
FEATURE            Location/Qualifiers
source             1..5
                   mol_type = protein
                   note = derivative peptide
                   organism = synthetic construct
```

```
SEQUENCE: 14
WYNGK                                                                          5

SEQ ID NO: 15          moltype = AA  length = 5
FEATURE                Location/Qualifiers
source                 1..5
                       mol_type = protein
                       note = derivative peptide
                       organism = synthetic construct
SEQUENCE: 15
WYQGK                                                                          5

SEQ ID NO: 16          moltype = AA  length = 5
FEATURE                Location/Qualifiers
source                 1..5
                       mol_type = protein
                       note = derivative peptide
                       organism = synthetic construct
SEQUENCE: 16
WYTGK                                                                          5

SEQ ID NO: 17          moltype = AA  length = 5
FEATURE                Location/Qualifiers
source                 1..5
                       mol_type = protein
                       note = derivative peptide
                       organism = synthetic construct
SEQUENCE: 17
WYDGK                                                                          5

SEQ ID NO: 18          moltype = AA  length = 5
FEATURE                Location/Qualifiers
source                 1..5
                       mol_type = protein
                       note = derivative peptide
                       organism = synthetic construct
SEQUENCE: 18
WYYGK                                                                          5

SEQ ID NO: 19          moltype = AA  length = 5
FEATURE                Location/Qualifiers
source                 1..5
                       mol_type = protein
                       note = derivative peptide
                       organism = synthetic construct
SEQUENCE: 19
WYRGK                                                                          5

SEQ ID NO: 20          moltype = AA  length = 5
FEATURE                Location/Qualifiers
source                 1..5
                       mol_type = protein
                       note = derivative peptide
                       organism = synthetic construct
SEQUENCE: 20
WYHGK                                                                          5
```

What is claimed is:

1. A high-activity memory-improving derivative peptide, having an amino acid sequence selected from the group consisting of:

Trp-Tyr-Glu-Gly-Lys (WYEGK) (SEQ ID NO: 2), Trp-Tyr-Lys-Gly-Lys (WYKGK) (SEQ ID NO: 3), Trp-Tyr-Ser-Gly-Lys (WYSGK) (SEQ ID NO: 4), and Trp-Tyr-Phe-Gly-Lys (WYFGK) (SEQ ID NO: 5).

2. The high-activity memory-improving derivative peptide according to claim 1, wherein through Morris water maze for scopolamine-induced memory impairment model mice, escape latency decreases from 70.74 s to 35.78-40.53 s, percent time spent in target quadrant increases from 24.24% to 32.19-36.22%, and frequency of platform crossing increases from 1.1 times to 3.1-3.8 times in mice of each of derivative peptide treatment groups compared with a model group.

3. The high-activity memory-improving derivative peptide according to claim 1, wherein an antioxidant capacity of the derivative peptide is determined by ABTS free radical scavenging assay and oxygen radical antioxidant capacity (ORAC) assay; at a concentration of 100 μM, ABTS free radical scavenging rate of the WYEGK (SEQ ID NO: 2), the WYKGK (SEQ ID NO: 3), the WYEGK SEQ ID NO: 4), and the WYFGK (SEQ ID NO: 5) reaches 54.48%, 40.31%, 70.47%, and 36.56%, respectively, and ORAC values thereof reach 5,422.29, 3,681.50, 5,473.16, and 3,762.05 μmol TE/g, respectively, indicating that the derivative peptide has high antioxidant activity.

4. The high-activity memory-improving derivative peptide according to claim 1, wherein stability of the derivative peptide is analyzed by pH stability, simulating gastric and intestinal digestion experiments; the derivative peptide is stable at pH 2 to 8, and retention rate of peptide content reaches at least 93.45% in simulated gastrointestinal digestion.

5. A memory-improving medicaments, health care products or food, comprising the high-activity memory-improving derivative peptide according to claim 1.

6. The memory-improving medicament, health care product or food according to claim 5, wherein through Morris water maze for scopolamine-induced memory impairment model mice, escape latency decreases from 70.74 s to 35.78-40.53 s, percent time spent in target quadrant increases from 24.24% to 32.19-36.22%, and frequency of platform crossing increases from 1.1 times to 3.1-3.8 times in mice of each of derivative peptide treatment groups compared with a model group.

7. The memory-improving medicament, health care product or food according to claim 5, wherein an antioxidant capacity of the derivative peptide is determined by ABTS free radical scavenging assay and oxygen radical antioxidant capacity (ORAC) assay; at a concentration of 100 μM, ABTS free radical scavenging rate of the WYEGK, the WYKGK, the WYSGK, and the WYFGK reaches 54.48%, 40.31%, 70.47%, and 36.56%, respectively, and ORAC values thereof reach 5,422.29, 3,681.50, 5,473.16, and 3,762.05 μmol TE/g, respectively, indicating that the derivative peptide has high antioxidant activity.

8. The memory-improving medicament, health care product or food according to claim 5, wherein stability of the derivative peptide is analyzed by pH stability, simulating gastric and intestinal digestion experiments; the derivative peptide is stable at pH 2 to 8, and retention rate of peptide content reaches at least 93.45% in simulated gastrointestinal digestion.

9. The memory-improving medicament, health care product or food according to claim 5, wherein the medicaments, health care products or foods comprises other memory-improving ingredients and/or acceptable excipients.

10. The memory-improving medicament, health care product or food according to claim 6, wherein the medicaments, health care products or foods comprises other memory-improving ingredients and/or acceptable excipients.

11. The memory-improving medicament, health care product or food according to claim 7, wherein the medicaments, health care products or foods comprises other memory-improving ingredients and/or acceptable excipients.

12. The memory-improving medicament, health care product or food according to claim 8, wherein the medicaments, health care products or foods comprises other memory-improving ingredients and/or acceptable excipients.

* * * * *